US006984658B2

(12) United States Patent
Rissanen et al.

(10) Patent No.: US 6,984,658 B2
(45) Date of Patent: Jan. 10, 2006

(54) OLIGO/POLYSUCCINIMIDES, PROCESS FOR PRODUCING THEREOF AND THEIR USE

(75) Inventors: Kari Rissanen, Hankasalmi (FI); Miikka Pakkala, Kuopio (FI); Salme Koskimies, Helsinki (FI); Sami Nummelin, Jyväskylä (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 266 days.

(21) Appl. No.: 10/257,274

(22) PCT Filed: Apr. 11, 2001

(86) PCT No.: PCT/FI01/00361

§ 371 (c)(1),
(2), (4) Date: Apr. 29, 2003

(87) PCT Pub. No.: WO01/79329

PCT Pub. Date: Oct. 25, 2001

(65) Prior Publication Data

US 2004/0049055 A1 Mar. 11, 2004

(30) Foreign Application Priority Data

Apr. 14, 2000 (FI) ................................. 20000894

(51) Int. Cl.
*A61K 31/4025* (2006.01)
*C07D 207/04* (2006.01)
(52) U.S. Cl. ...................................... 514/422; 548/546
(58) Field of Classification Search ................ 548/546; 514/422
See application file for complete search history.

(56) References Cited

U.S. PATENT DOCUMENTS

| | | |
|---|---|---|
| 3,154,560 A | 10/1964 | Osuch |
| 3,202,678 A | 8/1965 | Stuart et al. |
| 3,219,666 A | 11/1965 | Norman et al. |
| 3,306,907 A | 2/1967 | McNinch et al. |
| 3,342,735 A | 9/1967 | Reed et al. |
| 4,322,336 A | 3/1982 | Machurat et al. |
| 4,938,885 A | 7/1990 | Migdal |
| 4,997,594 A | 3/1991 | Walsh |
| 5,235,067 A | 8/1993 | Allen et al. |
| 5,266,186 A | 11/1993 | Kaplan |
| 5,484,945 A | 1/1996 | Nagatomo et al. |
| 5,556,575 A | 9/1996 | Babaian-Kibala et al. |
| 5,752,989 A | 5/1998 | Henly et al. |

FOREIGN PATENT DOCUMENTS

| | | |
|---|---|---|
| EP | 0271937 A2 | 6/1988 |
| EP | 0662504 A1 | 7/1995 |
| EP | 1120433 A1 | 8/2001 |
| JP | 9031197 A | 2/1997 |
| WO | WO 95/28460 A1 | 10/1995 |
| WO | WO 96/07688 A1 | 3/1996 |
| WO | WO97/00245 A1 | 1/1997 |
| WO | WO 00/75217 A1 | 12/2000 |

*Primary Examiner*—Taofiq Solola
(74) *Attorney, Agent, or Firm*—Birch, Stewart, Kolasch & Birch, LLP

(57) ABSTRACT

The invention is directed to oligo/polysuccinimides prepared from alkyl or alkenyl succinic anhydride, containing two or more imide groups, a method for producing such oligo-polysuccinimides, and the use thereof as dispersing agents in lubricant products, plasticizers in plastics, surface sizes for paper industry, reactive additives, for coating and composite applications, as well as encapsulating agents in pharmaceutical and speciality chemical products. In the method, a linear or branched $C_4$–$C_{24}$ alkyl or alkenyl succinic anhydride is reacted with an oligoamine having two or more primary amino groups to obtain the corresponding oligo/polysuccinimide.

15 Claims, No Drawings

OLIGO/POLYSUCCINIMIDES, PROCESS FOR PRODUCING THEREOF AND THEIR USE

This application is the national phase under 35 U.S.C. § 371 of PCT International Application No. PCT/FI01/00361 which has an International filing date of Apr. 11, 2001, which designated the United States of America.

The invention is directed to oligo/polysuccinimides prepared from alkyl or alkenyl succinic anhydride, containing two or more imide groups, a method for producing such oligo/polysuccinimides, and the use thereof as dispersing agents in lubricant products, plasticizers in plastics, surface sizes for paper industry, reactive additives, for coating and composite applications, as well as encapsulating agents in pharmaceutical and speciality chemical products.

A method for producing alkenyl, and particularly polyalkenyl imides and the use thereof as dispersing agents in oil and lubricant products are known from several publications. In various methods, the imide is prepared from alkenyl or polyalkenyl succinic anhydride in such a manner that a single primary amino group reacts to form a monoimide. Instead of an alkyl or alkenyl group, the amine starting material may also contain a hydroxyl group or a tertiary or a secondary amino group. For a diamine having two primary amino groups, the imide reaction is commonly optimized to allow only one of the amino groups to react, thus preventing the formation of deleterious, often solid polymerisation products, as is disclosed in U.S. Pat. No. 3,202,678. This publication presents, suitable as additives in lubricants, alkenyl succinimides substituted with N-polyamine, the alkenyl group being a $C_{30}$–$C_{200}$ polyolefin radical. Tetraethylene pentamine is the amine starting material for monoimide. U.S. Pat. No. 3,219,666 discloses succinimides substituted with polyisobutene, useful as dispersing agents in lubricants. Alkyl amines, and particularly polyalkylene polyamines are used as starting materials for these imides. U.S. Pat. No. 3,306,907 discloses the $N_1,N_5$-di(polybutenyl succinimides). The diimides, particularly suitable as additives for lubricants, are produced by reacting mono(polybutenyl succinic anhydride) with tetraethylene pentamine. Oligomers having a highly brached structure and a spherical shape are called dendrimers. WO 96/07688 publication presents some hyperbranched spherical (meth)acrylated polyesters that may be used in resins curable with UV light. Dendrimers having various structures are nowadays also commercial available.

In prior art methods for producing imides, the reactions are not particularly selective and accordingly, polymeric by-products are formed as impurities, causing such problems as hydrolysis and decomposition. Moreover, several of the products are monoimides having a free amino group often making the compounds more or less toxic. During the reaction, polymerization occurs frequently, the prevention thereof being, however, extremely difficult. In addition, for diimides, is is difficult to carry out the reaction symmetrically and selectively.

Based on above teachings, it is clear that there is an evident need for novel, pure oligo/polysuccinimides and methods for the production thereof.

The object of the invention is to provide oligo/polysuccinimides, a method for producing such oligo/polysuccinimides, and the use thereof.

The oligo/polysuccinimides of the invention, the method for producing such oligo/polysuccinimides, and the use thereof are charecterized in the claims.

Problems accompanying the prior art succinimides and the methods for their production may be avoided or substantially reduced with the solution of the invention. In the method of the invention, a linear or branched $C_4$–$C_{24}$, preferably $C_8$–$C_{20}$ alkyl or alkenyl succinic anhydride (ASA=alkyl or alkenyl succinic anhydride) is reacted with an oligoamine having two or more primary amino groups to obtain the corresponding oligoimide with high yield and selectivity. The $C_4$–$C_{24}$ alkyl or alkenyl succinic anhydride used as the starting material may be prepared with the known so-called ene reaction from linear or branched olefins, either internal or α-olefins, or from mixtures thereof by heating with maleic anhydride at 170 to 230° C. If necessary, the double bonds may be removed by hydrogenation according to any prior art method. The scheme 1 below shows by way of example the production of di-(R'-ASA)-imide of hexamethylene diamine starting from R'-ASA and hexamethylene diamine (HMDA). R' being a $C_{18}H_{35}$ monoolefin having a degree of linearity of more than 85%, the di-($C_{18}H_{35}$-ASA)-imide of HMDA is obtained.

Scheme 1
Production of di-(R'-ASA)-imide of hexamethylene diamine

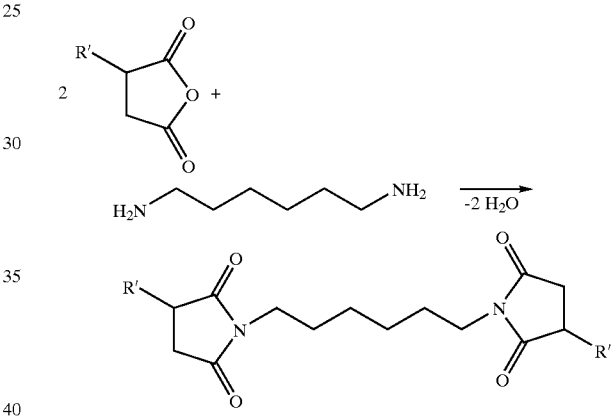

The method of the invention is now described in more detail. Oligo/polysuccinimides may be prepared by reacting a linear or branched $C_4$–$C_{24}$, preferably $C_8$–$C_{20}$ alkyl or alkenyl succinic anhydride with an oligoamine such as diamine ($H_2N$—$(CH_2)_m$—$NH_2$, wherein m=6, 11 or 12), tetraethylene pentamine (TEPA), hexamethylene diamine (HMDA), or diaminobutane oligoethyleneamine (DAB (AM)$_n$, wherein n=4, 8, 16 or 32), the ASA to amine molar ratio being n:1, wherein n is the number of primary amino groups in oligoamine, in the presence or absence of a solvent, at the temperature of 100 to 190° C., the reaction time being from 3 to 6 hours. As a catalyst, an acid catalyst, preferably para-toluene sulphonic acid is used in an amount from 0.1 to 1%, by weight, or the reaction may also be carried out without a catalyst. Suitable solvents include aromatic solvents, e.g. toluene or xylene, or solvent mixtures. The reaction is followed by the removal of the solvent and unreacted starting compounds in a suitable manner, for instance with vacuum distillation. The products obtained are viscous liquids, even in the case the molecular weights of the products are between 2000 and 10,000. The yields of the reactions are high, up to 95%. The desired oligoimides are obtained very selectively with this method.

By way of example, Schemes 2, 3 and 4 show the production of some other oligo/polysuccinimides of the invention. Scheme 2 shows the preparation of di-($C_{18}$-

ASA)-imide of tetraethylene pentamine (TEPA), Scheme 3 shows the preparation of tetra-($C_{18}$-ASA)-imide from diaminobutane tetraethyleneamine (DAB(AM)$_4$), and Scheme 4 shows the preparation of octa-($C_{18}$-ASA)-imide from diaminobutane octaethyleneamine (DAB(AM)$_8$). In these examples, R' is a linear $C_{18}H_{35}$-monoolefin having a linearity of more than 85%.

Scheme 2
Preparation of di-($C_{18}$-ASA)-imide of (TEPA),
i.e. $N_1,N_5$-di-($C_{18}$-ASA)-imide of tetraethylene pentamine where n=3.

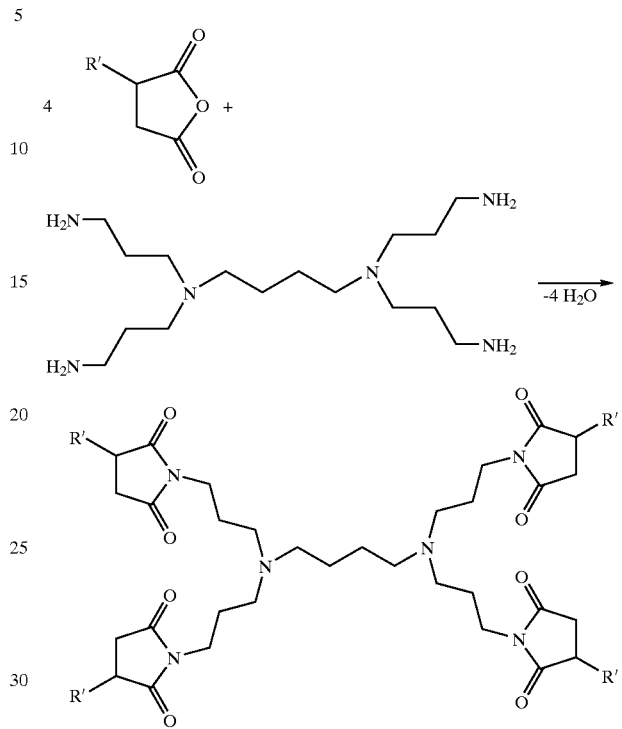

Scheme 3
Preparation of tetra-($C_{18}$-ASA)-imide of (DAB(AM)$_4$)

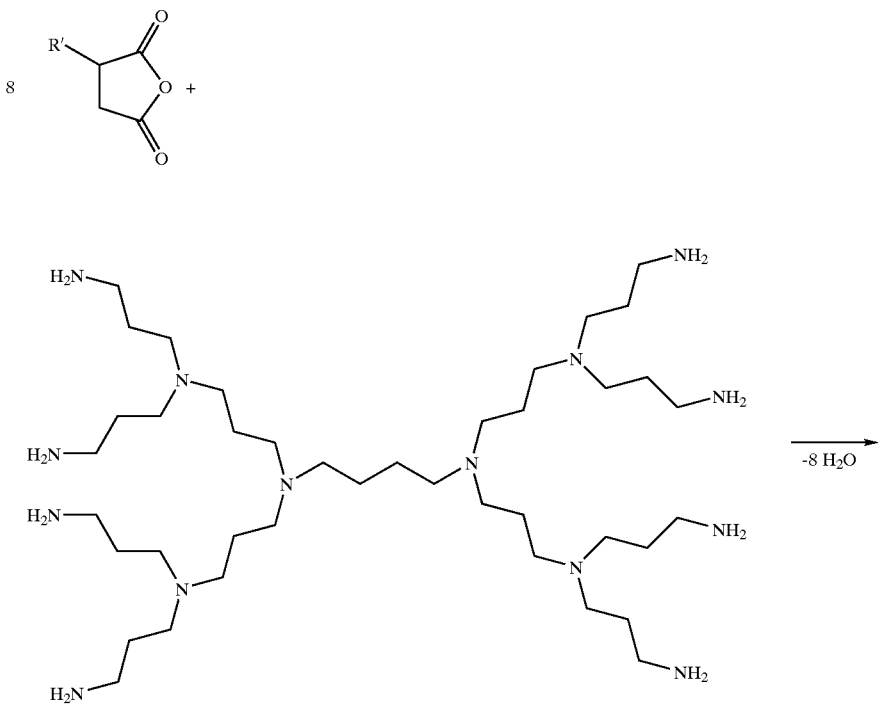

Scheme 4
Preparation of octa-($C_{18}$-ASA)-imide of (DAB(AM)$_8$)

-continued

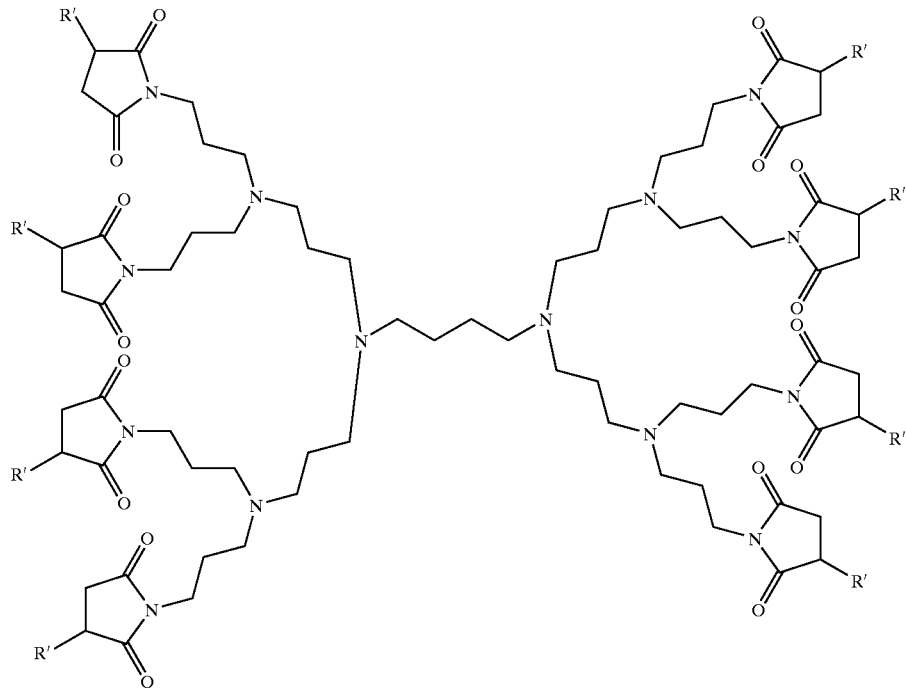

From the above schemes it may be seen that some of the oligo/polysuccinimides of the invention have a dendritic structure. Surprisingly, the viscosities of these macro-molecular dendrimers will not increase substantially although the molecular weight of the imide is multiplied. This exceptional dendritic structure and the properties resulting therefrom make the compounds of the invention applicable in a versatile manner to various purposes including the use as dispersing agents in oil and lubricant products, aids such as plasticizers in plastics, surface sizes for paper industry, reactive additives, and in coating and composite materials. The amino structure of the inner shell or core of the compounds allows the encapsulation of metals or drugs in these molecules. Moreover, since the hydrocarbon moiety of the outer shell of the product is strongly hydrophobic, it effectively slows down the penetration of water towards the inner shell, thus protecting the substances encapsulated therein.

The method of the invention is characterized by a reaction that is clearly more selective than that of the prior art methods. Moreover, in the method of the invention, the desired products containing no impurities that might catalyze decomposing reactions during final use thereof are obtained selectively and with surprisingly high yields from the starting materials in a single step. Further, the products are polymeric compounds without any free amino groups, and thus they are generally non-toxic. By means of the reaction, even molecules of very high molecular weight such as dendrimers are symmetrically obtained without any undesirable polymerization in the reaction. The viscous liquid products of high molecular weight are also excellently suitable as aids in paints, as plasticizers and as corrosion inhibitors due to their metal encapsulating properties. Moreover, the compounds may be used for catalytic purposes. The molecules of the invention may also be used for encapsulating drugs and speciality chemicals, since the outer shells of said compounds are hydrophobic, the inner parts being polar. In such cases the applications include drugs with sustained action, printing inks and the like.

The invention will now be illustrated by means of the following examples. It is clear for those skilled in the art that the invention is not meant to be limited solely to these examples but several variations are possible within the spirit and scope of the inventive idea.

EXAMPLE 1

Production of di-($C_{18}$-ASA)-imide of HMDA

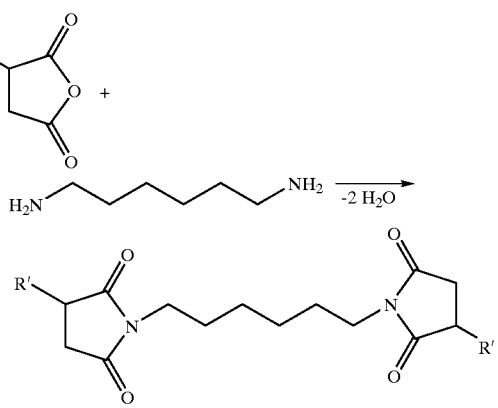

0.04 moles (4.65 g) of hexamethylene diamine (HMDA) was added to a three-neck flask equipped with a vertical condenser, and 0.08 moles (28.04 g) of $C_{18}$-ASA was dropped thereto during 25 minutes at 20 to 28° C. under constant mixing. Nitrogen stream was connected and vigorous mixing started. The mixture was heated in an oil bath at 135 to 170° C., refluxing it for 6 hours. Water formed in the reaction evaporated and was condensed in water recovery intermediate part. Unreacted HMDA was removed by vacuum distillation (at about 90° C./3 to 14 mmHg). Yield: 27.35 g; 88.5%. $^1$H-NMR-spectrum showed the product to be rather pure imide.

EXAMPLE 2

Production of di-($C_{18}$-ASA)-imide of HMDA 2.54 g (0.022 moles) of HMDA and 10 ml of xylene were added to a three-neck flask equipped with a vertical condenser. 15.34 g of $C_{18}$-ASA in 15 ml of xylene were dropped during 15 minutes to the reaction mixture at 42 to 90° C. under constant mixing. The mixture was refluxed at 135 to 142° C. for 6 hours. The solvent and excess of HMDA were removed by vacuum distillation. Imide yield: 11.4 g, 90.2%. $^1$H-NMR-spectrum showed the product to be the desired imide.

EXAMPLE 3

Production of di-($C_{18}$-ASA)-imide of TEPA

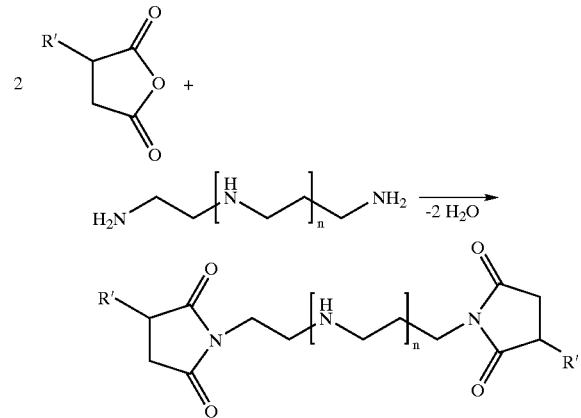

where n=3

The synthesis was carried out as in Example 1 by using 0.025 moles (4.733 g) of tetraethylene pentamine (TEPA) and 0.050 moles (17.527 g) of $C_{18}$-ASA as starting materials. Unreacted TEPA was removed by vacuum distillation. Imide yield: 19.55 g, 92.9%. $^1$H-NMR-spectrum showed the product to be the desired imide.

EXAMPLE 4

Production of tetra-($C_{18}$-ASA)-imide of DAB(AM)$_4$

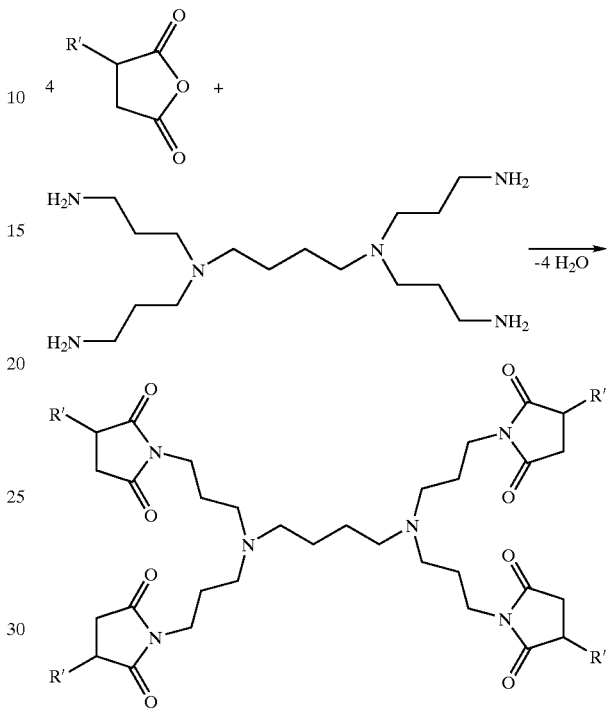

The synthesis was carried out as in Example 1, by adding 0.005 moles (1.58 g) of DAB(AM)$_4$, 0.020 moles (7.01 g) of $C_{18}$-ASA and raising the temperature to 100° C. under vigorous mixing. Thereafter the mixture was heated under nitrogen atmosphere at a temperature of 150 to 170° C. in an oil bath for 6 hours. Water formed was thus removed. Imide yield: 8.25 g, 89.7% as viscous yellowish liquid. $^1$H-NMR-spectrum showed the product to be the desired imide.

EXAMPLE 5

Production of octa-($C_{18}$-ASA)-imide of DAB(AM)$_8$

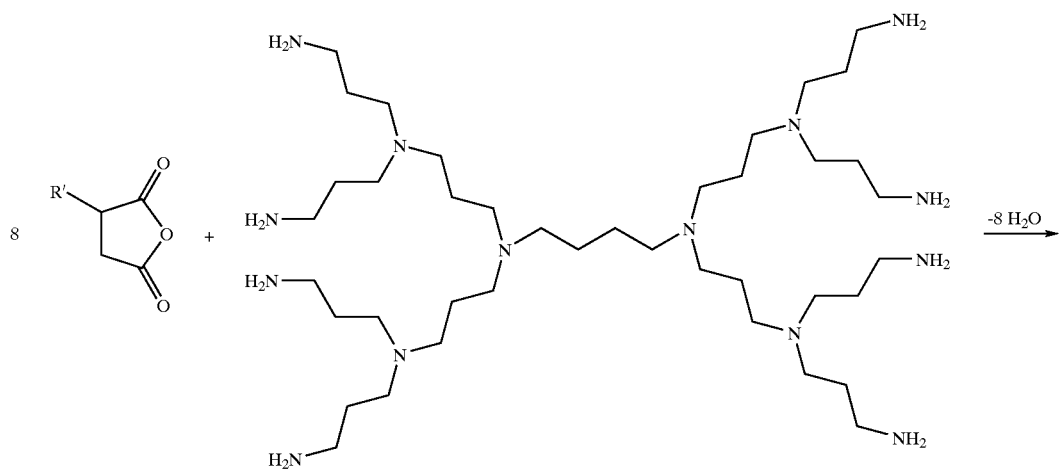

-continued

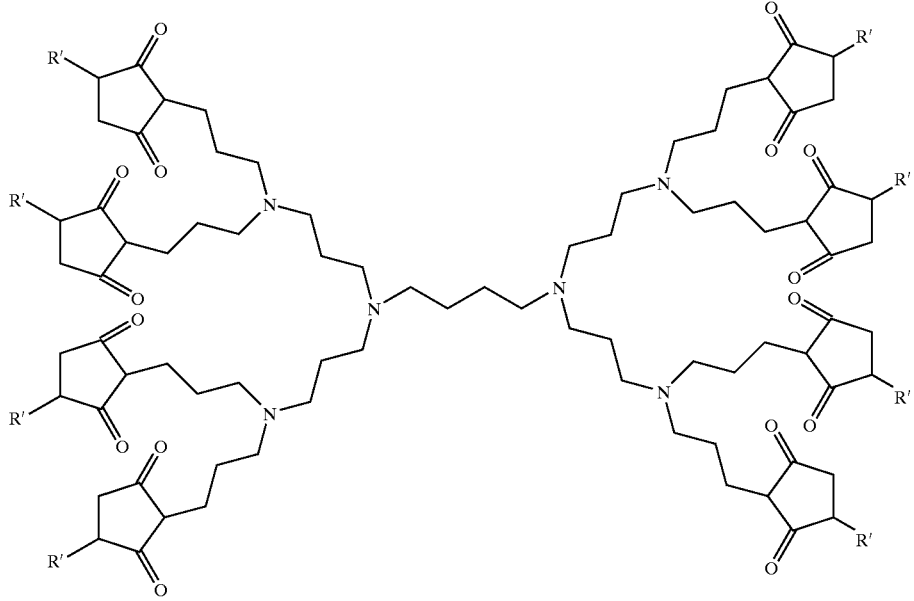

The synthesis was carried out as in Example 4. The starting materials were 0.003 moles (2.32 g) of DAB(AM)$_8$ and 0.024 moles (8.41 g) of $C_{18}$-ASA. Imide yield: 10.3 g, 85.2% as viscous yellowish liquid. $^1$H-NMR-spectrum showed the product to be the desired imide.

The following examples 6 and 7 show the preparation of hexadeca-($C_{18}$-ASA)-imide of DAB(AM)$_{16}$ and 32-($C_{18}$-ASA)-imide of DAB(AM)$_{32}$. Reaction equations and structures of final products are analogous to those presented in examples 4 and 5. The starting amine contains either 16 (Ex. 6) or 32 (Ex. 7) primary amino groups, the product containing either 16 or 32 ASA-imide groups, respectively.

EXAMPLE 6

Production of hexadeca-($C_{18}$-ASA)-imide of DAB(AM)$_{16}$

The synthesis was carried out by adding 16 mmoles (5,61 g) of $C_{18}$-ASA to the reaction vessel, temperature was raised to 120° C., then 1 mmole (1.69 g) of DAB(AM)$_{16}$ was added during about 10 minutes to the mixture, temperature was raised to 160° C., and the compounds were allowed to react for about 5 to 6 hours, during which the water formed was removed. $^1$H-NMR-spectrum showed that the desired polyimide was formed with nearly stoichiometric yield. The product was a viscous yellowish liquid.

EXAMPLE 7

Production of 32-($C_{18}$-ASA)-imide of DAB(AM)$_{32}$

The synthesis was carried out as in Example 1 by adding the starting materials, i.e. 1 mmole (3.5 g) of DAB(AM)$_{32}$ and 32 mmoles (11.22 g) of $C_{18}$-ASA to the reaction vessel. The mixture was allowed to react at 140° C. for about 6 hours. $^1$H-NMR-spectrum showed that the desired polyimide was formed with nearly stoichiometric yield. The product was a viscous yellowish liquid.

What is claimed is:

1. A method for producing oligo/polysuccinimides, comprising:
    reacting a linear or branched $C_4$–$C_{24}$ alkyl or alkenyl succinic anhydride with a diaminobutane oligoethyleneamine DAB(AM)$_n$, wherein n=4, 8, 16 or 32 and having 4, 8, 16 or 32 primary amino groups to obtain the corresponding oligo/polysuccinimide.

2. The method according to claim 1, wherein said alkyl or alkenyl succinic anhydride is a $C_8$–$C_{20}$ alkyl or alkenyl succinic anhydride.

3. The method according to claim 1 or 2, wherein the molar ratio of alkyl or alkenyl succinic anhydride to oligoamine is n:1 and n being the number of the primary amino groups in the oligoamine.

4. The method according to claim 1, wherein the oligo/polysuccinimide has a dendritic structure.

5. The method according to claim 1, wherein the reaction is carried out at a temperature between 100 and 190° C. in the presence or absence of a catalyst, and in the presence or absence of a solvent.

6. The method according to claim 1, wherein said catalyst is used in an mount of 0.1 to 1% by weight, the catalyst being para-toluene sulphonic acid and the solvent being an aromatic solvent or a mixture of solvents.

7. An oligo/polysuccinimide which is a (linear or branched $C_4$–$C_{24}$ alkyl or alkenyl) succinimide of a diaminobutane oligoethyleneamine DAB(AM)$_n$, wherein n=4, 8, 16 or 32 and having 4, 8, 16 or 32 primary amino groups.

8. The oligo/polysuccinimide according to claim 7, wherein said alkyl or alkenyl succinimide is a ($C_8$–$C_{20}$ alkyl or alkenyl) succinimide.

9. The oligo/polysuccinimide according to claim 7 or 8, wherein the oligo/polysuccinimide has a dendritic structure.

10. The oligo/polysuccinimide according to claim 7, wherein the oligo/polysuccinimide is selected from tetra-($C_{18}$-alkyl or alkenyl) succinimide of diaminobutane tetraethyleneamine DAB(AM)$_4$, octa-($C_{18}$-alkyl or alkenyl) succinimide of diaminobutane octaethyleneamine DAB(AM)$_8$, hexadeca-($C_{18}$-alkyl or alkenyl) succinimide of diaminobutane hexadecathyleneamine DAB(AM)$_{16}$ and 32-($C_{18}$-alkyl or alkenyl) succinimide of diaminobutane ethyleneamine DAB(AM)$_{32}$.

11. A lubricant or oil composition, comprising:
the oligo/polysuccinimide according to claim 7 or prepared with the method according to claim 1, as a dispersing agent; and
a lubricant or oil base.

12. The method according to claim 1, wherein the hydrocarbon moiety is a $C_{18}H_{35}$ monoolefin having a linearity of 85%.

13. The oligo/polysuccinimide according to claim 7, wherein the hydrocarbon moiety is a $C_{18}H_{35}$ monoolefin having a linearity of 85%.

14. A composition, comprising:
the oligo/polysuccinimide according to claim 7 or prepared with the method according to claim 1, as an additive; and
a plastic, coating, catalyst or composite material in admixture therewith.

15. A composition, comprising:
the oligo/polysuccinimide according to claim 7 or prepared with the method according to claim 1, as an encapsulating agent; and
a metal, drug, printing ink or specialty material encapsulated therewith.

* * * * *